(12) United States Patent
Pockaj et al.

(10) Patent No.: US 11,060,150 B2
(45) Date of Patent: Jul. 13, 2021

(54) METHODS AND MATERIALS FOR ASSESSING AND TREATING CANCER

(71) Applicant: Mayo Foundation for Medical Education and Research, Rochester, MN (US)

(72) Inventors: Barbara A. Pockaj, Scottsdale, AZ (US); Michael T. Barrett, Scottsdale, AZ (US); Mitesh J. Borad, Tempe, AZ (US); Karen S. Anderson, Phoenix, AZ (US); Ramesh K. Ramanathan, Paradise Valley, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/558,611

(22) PCT Filed: Mar. 16, 2016

(86) PCT No.: PCT/US2016/022618
§ 371 (c)(1),
(2) Date: Sep. 15, 2017

(87) PCT Pub. No.: WO2016/149350
PCT Pub. Date: Sep. 22, 2016

(65) Prior Publication Data
US 2018/0080085 A1 Mar. 22, 2018

Related U.S. Application Data

(60) Provisional application No. 62/134,188, filed on Mar. 17, 2015.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 7,794,710 B2 | 9/2010 | Chen et al. | |
| 8,981,063 B2 | 3/2015 | Chen et al. | |
| 9,803,015 B2 | 10/2017 | Chen et al. | |
| 2015/0071910 A1* | 3/2015 | Kowanetz | C07K 16/30 424/133.1 |
| 2015/0210769 A1* | 7/2015 | Freeman | A61P 1/04 424/136.1 |
| 2015/0259420 A1* | 9/2015 | Triebel | C07K 16/2803 424/136.1 |
| 2017/0175197 A1* | 6/2017 | Gatalica | G06F 19/325 |

FOREIGN PATENT DOCUMENTS

| | | |
|---|---|---|
| EP | 2650682 | 10/2013 |
| WO | WO 2013/112942 | 8/2013 |
| WO | WO 2014/151290 | 9/2014 |

OTHER PUBLICATIONS

Garber (JNCI 2011 vol. 103 p. 1079) (Year: 2011).*
Steidl et al. (Nature 2011 vol. 471 p. 377) (Year: 2011).*
Miller et al. (Cancer Immunol Res Jan. 15, 2014 vol. 2 p. 301-306) (Year: 2014).*
Grigoriadis et al. (BMC Genomics 2012 vol. 13 p. 619) (Year: 2012).*
Balko et al., "JAK2 amplifications are enriched in triple negative breast cancers (TNBCs) after neoadjuvant chemotherapy and predict poor prognosis," Abstract S6-01, Dec. 2013.
Chase et al., "Ruxolitinib as potential targeted therapy for patients with JAK2 rearrangements," Haematologica, 98(3):404-8, Mar. 2013.
Extended European Search Report in European Application No. 16765644.6, dated Oct. 5, 2018, 122 pages.
Hao et al., "Selective JAK2 inhibition specifically decreases Hodgkin lymphoma and mediastinal large B-cell lymphoma growth in vitro and in vivo," Clinical Cancer Research, clincanres-3007, Mar. 2014.
Anderson et al., "High-level amplification of chromosome 9p24 targeting PD-L1 and JAK2 correlates with worse DFS and OS in triple negative breast cancer," AACR.org [online] Mar. 18, 2015 [retrieved on Apr. 6, 2015]. Retrieved from the Internet: <URL: http://www.abstractsonline.com/Plan/ViewAbstract.aspx?mID=3682&sKey=72104ef5-2237-46d6-a1a5-403333deb391&cKey=8a09af77-c133-466b-a861-d49de8c73263&mKey=19573a54-ae8f-4e00-9c23-bd6d62268424>, 2 pages [presentation abstract 2861].
Ansell et al., "PD-1 Blockade with Nivolumab in Relapsed or Refractory Hodgkin's Lymphoma," *NEJM.*, 372(4):311-319, 2015.
Balko et al, "Molecular profiling of the residual disease of triple-negative breast cancers after neoadjuvant chemotherapy identifies actionable therapeutic targets," *Cancer Discov.*, 4(2):232-245, Feb. 2014.
Barrett et al., "Genomic amplification of 9p24.1 targeting JAK2, PD-L1, and PD-L2 is enriched in high-risk triple negative breast cancer," *Oncotarget.*, 6(28):26483-26493, Jul. 3, 2015.
Basu et al., "Prevalence of KRAS, BRAF, NRAS, PIK3CA, and PTEN alterations in colorectal cancer: Analysis of a large international cohort of 5,900 patients," *Journal of Clinical Oncology.*, Jan. 20, 2014 32:3_suppl, Abstract 399, Retrieved Aug. 3, 2018, Retrieved Online: URL <http://ascopubs.org/doi/abs/10.1200/jco.2014.32.3_suppl.399>, 2 pages.

(Continued)

*Primary Examiner* — Katherine D Salmon
(74) *Attorney, Agent, or Firm* — Fish & Richardson P.C.

(57) ABSTRACT

This document provides methods and materials involved in assessing cancer (e.g., breast cancer). For example, methods and materials for determining whether or not a cancer patient (e.g., a breast cancer patient) having ER−/PgR−/HER2− cancer cells is likely to have a favorable or unfavorable outcome and/or is likely to respond a cancer treatment that includes a PD-1 inhibitor and/or PD-L1 inhibitor in combination with a JAK2 inhibitor are provided. Methods and materials involved in treating mammals having ER−/PgR−/HER2− cancer (e.g., ER−/PgR−/HER2− breast cancer) by administering a PD-1 inhibitor and/or PD-L1 inhibitor in combination with a JAK2 inhibitor also are provided.

7 Claims, 13 Drawing Sheets

(56) References Cited

OTHER PUBLICATIONS

Bayraktar and Glück, "Molecularly targeted therapies for metastatic triple-negative breast cancer," *Breast Cancer Res Treat.*, 138(1):21-35. Epub Jan. 29, 2013.

Britschgi et al., "JAK2/STAT5 inhibition circumvents resistance to PI3K/mTOR blockade: a rationale for cotargeting these pathways in metastatic breast cancer," *Cancer Cell.*, 22(6):796-811, Dec. 11, 2012.

Cancer Genome Atlas Research Network, "Comprehensive molecular characterization of gastric adenocarcinoma," *Nature.*, 513(7517):202-209, Epub Jul. 23, 2014.

Chawla et al., "Immune checkpoints: A therapeutic target in triple negative breast cancer," *Oncoimmunology*, 3(3):e28325, 3 pages, Epub Apr. 8, 2014.

Emens et al "Inhibition of PD-L1 by MPDL3280a leads to clinical activity in patients with metastatic triple-negative breast cancer," Abstract presented at San Antonio Breast Cancer Symposium, Dec. 9-13, 2014, San Antonio, TX, USA, *Canc Res.*, 75(9 Suppl), May 2015, Retrieved Aug. 3, 2018, Retreived Online: URL <http://cancerres.aacrjournals.org/content/75/9_supplement/pd1-6>, 2 pages.

Galipeau et al., "NSAIDs Modulate CDKN2A, TP53, and DNA Content Risk for Progression to Esophageal Adenocarcinoma," *PLoS Med.*, 4(2):e67, Feb. 27, 2007.

Gatalica et al., "Programmed cell death 1 (PD-1) and its ligand (PD-L1) in common cancers and their correlation with molecular cancer type," *Cancer Epidemiol Biomarkers Prev.*, 23(12):2965-2970, Epub Nov. 12, 2014.

Green et al., "Integrative analysis reveals selective 9p24.1 amplification, increased PD-1 ligand expression, and further induction via JAK2 in nodular sclerosing Hodgkin lymphoma and primary mediastinal large B-cell lymphoma," *Blood*, 116(17):3268-3277, Epub Jul. 13, 2010.

Holley et al., "Deep Clonal Profiling of Formalin Fixed Paraffin Embedded Clinical Samples," *PLoS One.*, 7(11):e50586, Nov. 2012, 11 pages.

Inman, "Pembrolizumab Elicits Antitumor Responses in TNBC," OncLive [online] Dec. 10, 2014 [retrieved Apr. 6, 2018], Retrieved from the Internet: <URL: https://www.onclive.com/conference-coverage/sabcs-2014/pembrolizumab-elicits-antitumor-responsesin-tnbc>, 4 pages.

International Preliminary Report on Patentability for Application No. PCT/US2016/022618, dated Sep. 28, 2017, 7 pages.

International Search Report and Written Opinion in International Application No. PCT/US2016/22618, dated Jun. 3, 2016, 8 pages.

Lipson et al., "Efficient calculation of interval scores for DNA copy number data analysis," *J Comput Biol.*, 13(2):215-228, Mar. 2006.

Maley et al., "Genetic clonal diversity predicts progression to esophageal adenocarcinoma," *Nat Genet.*, 38(4):468-473, Mar. 26, 2006.

Mittendorf et al., "PD-L1 expression in triple-negative breast cancer," *Cancer Immunol Res.*, 2(4):361-370, Apr. 2014.

Nanda et al., "A phase Ib study of pembrolizumab (MK-3475) in patients with advanced triple-negative breast cancer," In: Proceedings of the Thirty-Seventh Annual CTRC-AACR San Antonio Breast Cancer Symposium: Dec. 9-13, 2014; San Antonio, TX. Philadelphia (PA): AACR; *Cancer Res.*, 75(9 Suppl):Abstract S1-09, May 2015, Retrieved Aug. 3, 2018, Retrieved Online: URL <http://cancerres.aacrjournals.org/content/75/9_Supplement/S1-09>, 2 pages.

Piscuoglio et al., "Integrative genomic and tmnscriptomic characterization of papillary carcinomas of the breast," *Mol Oncol.*, 8(8):1588-1602, Dec. 2014.

Przybytkowski et al., "Chromosome-breakage genomic instability and chromothripsis in breast cancer," *BMC Genomics.*, 15:579, 2014.

Rabinovitch et al., "Predictors of progression in Barrett's esophagus III: baseline flow cytometric variables," *Am J Gastroenterol.*, 96(11):3071-3083, Nov. 2001.

Ruiz et al., "Advancing a clinically relevant perspective of the clonal nature of cancer," *PNAS USA.*, 108(29):12054-12059, Jul. 19, 2011.

Thompson et al., "Tumor B7-H1 is associated with poor prognosis in renal cell carcinoma patients with long-term follow0up," *Canc Res.*, 66(7):3381-3385, Apr. 1, 2006.

Wu et al., "Identification and functional analysis of 9p24 amplified genes in human breast cancer," *Oncogene*, 31(3):333-341, Epub Jun. 13, 2011.

Han et al., "DNA Copy Number Alterations and Expression of Relevant Genes in Triple-Negative Breast Cancer," Genes, Chromosomes and Cancer, 47(6):490-499, Jun. 2008.

Ly et al., "Gene copy number variations in breast cancer of Sub-Saharan African women," The Breast, 22(3):295-300, Jun. 2013.

* cited by examiner

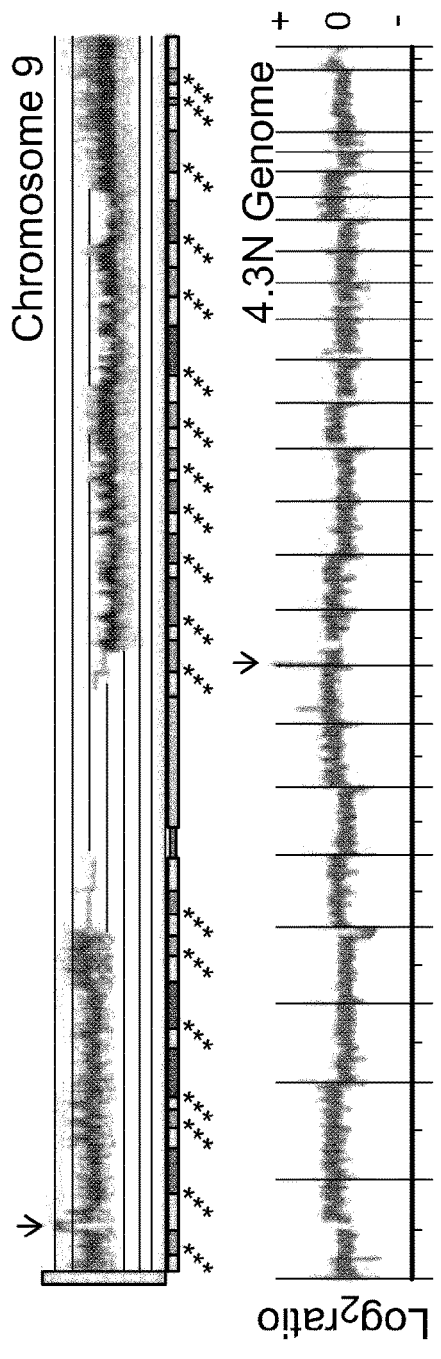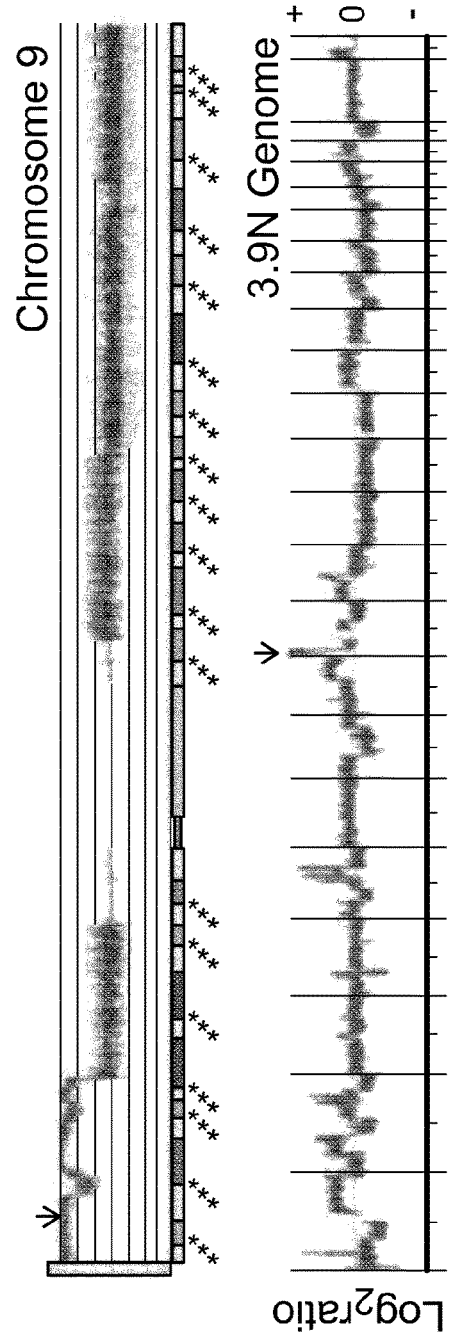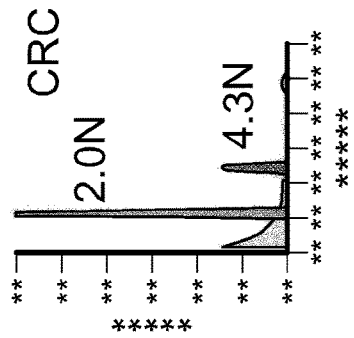
FIG. 1A
FIG 1B

PDJ Amplicon in TNBC

| TNBC Samples | 9p24.1 Score[a] |
|---|---|
| Mayo-847 | 3 |
| Mayo-469 | 1 |
| Mayo-648 | 1 |
| Mayo-787 | 1 |
| Mayo-462 | 1 |
| SAM592 | 1 |
| BAR588 | 1 |
| PAL598 | 1 |
| MEL589 | 1 |
| EBE486 | 1 |
| HOR675 | 1 |
| WON695 | 2 |
| CAM677 | 1 |
| HAY686 | 1 |
| DES588 | 1 |
| STE595 | 1 |
| DAV496 | 4 |
| Mayo517 | 0 |
| Mayo544 | 0 |
| Mayo628 | 0 |
| DON595 | 3 |
| RAO590 | 0 |
| HAR577 | 0 |
| JAR695 | 0 |
| 0143-001-3 | 3 |
| IBC 11 | 2 |
| IBC 9 A5 | 2 |
| THO 439 | 3 |
| BUC 589 | 2 |
| IBC 20 | 2 |
| GAS 353 | 0 |
| RUN 693 | 0 |

[a]Scores: 0 no change. 1 $\log_2$ratio >0 & <1.2 $\log_2$ratio >1 <2. 3 $\log_2$ratio >2 <3. 4 $\log_2$ratio $\geq$4

FIG. 4

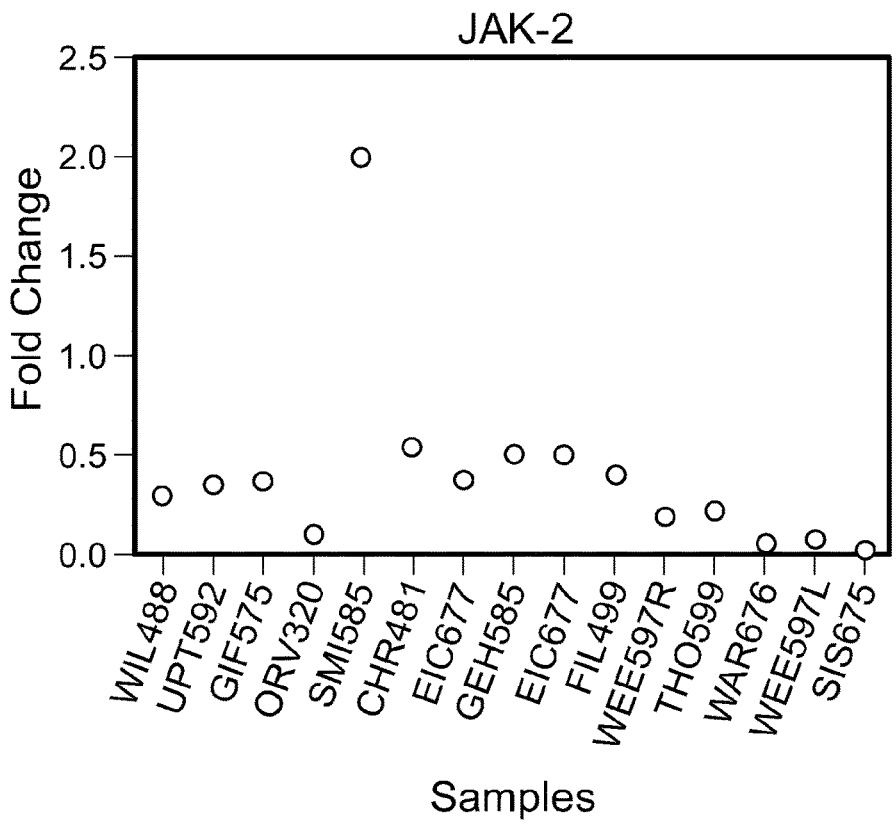
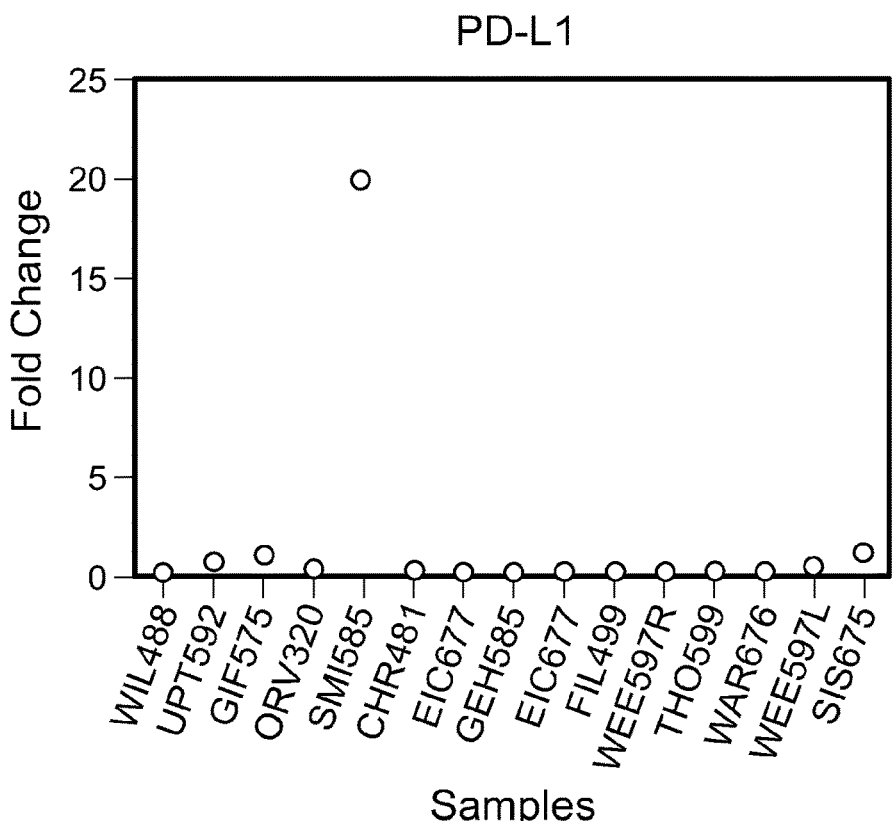
FIG. 5

Table 1
Comparison between patients with and without PDJ amplification

| | Not Amplified (N=28) | Amplified (N=8) | Total (N=36) | p value |
|---|---|---|---|---|
| Age [years] | | | | 0.79[1] |
| Mean (SD) | 53.4 (12.88) | 54.8 (8.71) | 53.7 (11.98) | |
| Median | 54.0 | 53.5 | 54.0 | |
| Range | (29.0-78.0) | (45.0-72.0) | (29.0-78.0) | |
| Tumor Size [cm] | | | | 0.04[1] |
| Mean (SD) | 1.9 (0.86) | 3.9 (3.88) | 2.4 (2.11) | |
| Median | 1.9 | 2.5 | 2.0 | |
| Range | (0.5-4.0) | (0.4-11.0) | (0.4-11.0) | |
| Grade | | | | 0.63[2] |
| 1 | 1 (3.6%) | 0 (0%) | 1 (2.8%) | |
| 2 | 7 (25%) | 1 (12.5%) | 8 (22.2%) | |
| 3 | 20 (71.4%) | 7 (87.5%) | 27 (75%) | |
| Lymphocytic Infiltrates | | | | 0.21[2] |
| Missing | 10 (.%) | 2 (.%) | 12 | |
| No | 14 (77.8%) | 6 (100%) | 20 (83.3%) | |
| Yes | 4 (22.2%) | 0 (0%) | 4 (16.7%) | |
| Lymph Nodes | | | | 0.01[2] |
| Missing | 1 (.%) | 0 (.%) | 1 | |
| Negative | 20 (74.1%) | 2 (25%) | 22 (62.9%) | |
| Positive | 7 (25.9%) | 6 (75%) | 13 (37.1%) | |
| Cancer Stage | | | | 0.04[2] |
| Missing | 1 (.%) | 0 (.%) | 1 | |
| Stage I | 11 (40.7%) | 1 (12.5%) | 12 (34.3%) | |
| Stage II | 13 (48.1%) | 3 (37.5%) | 16 (45.7%) | |
| Stage III | 3 (11.1%) | 4 (50%) | 7 (20%) | |
| Surgical Treatment | | | | 0.70[2] |
| Missing | 9 (.%) | 2 (.%) | 11 | |
| Breast Conservation Therapy (BCT) | 8 (42.1%) | 2 (33.3%) | 10 (40%) | |
| Mastectomy | 11 (57.9%) | 4 (66.7%) | 15 (60%) | |
| Chemotherapy | | | | 0.10[2] |
| Neoadjuvant | 1 (3.6%) | 2 (25%) | 3 (8.3%) | |
| No | 4 (14.3%) | 0 (0%) | 4 (11.1%) | |
| Yes | 23 (82.1%) | 6 (75%) | 29 (80.6%) | |
| Radiation [Mastectomy only] | | | | 0.88[2] |
| Missing | 17 (.%) | 4 (.%) | 21 | |
| No | 5 (45.5%) | 2 (50%) | 7 (46.7%) | |
| Yes | 6 (54.5%) | 2 (50%) | 8 (53.3%) | |

[1]Two-Sample T-Test [2]Chi-Square

FIG. 6

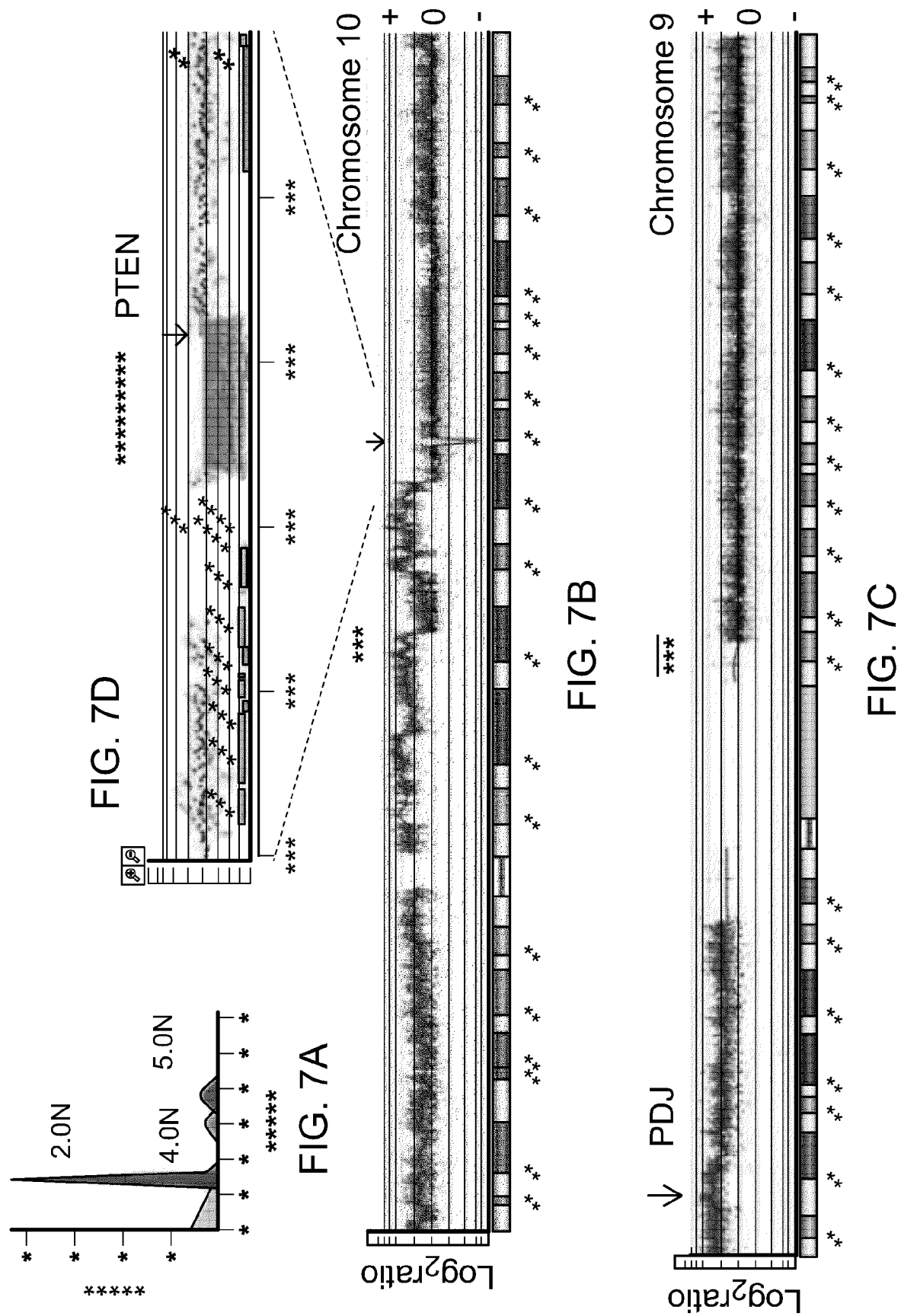

METHODS AND MATERIALS FOR ASSESSING AND TREATING CANCER

CROSS REFERENCE TO RELATED APPLICATIONS

This application is a National Stage application under 35 U.S.C. § 371 of International Application No. PCT/US2016/022618, having an International Filing Date of Mar. 16, 2016, which claims the benefit of U.S. Provisional Ser. No. 62/134,188 filed Mar. 17, 2015. These disclosures of the prior applications are considered part of (and are incorporated by reference in) the disclosure of this application.

BACKGROUND

1. Technical Field

This document relates to methods and materials involved in assessing cancer (e.g., breast cancer). For example, this document provides methods and materials for determining whether or not a cancer patient (e.g., a breast cancer patient) having estrogen receptor negative ($ER^-$), progesterone receptor negative ($PgR^-$), and human epidermal growth factor receptor 2 negative ($HER2^-$) cancer cells is likely to have a favorable or unfavorable outcome and/or is likely to respond to a cancer treatment that includes a PD-1 inhibitor and/or PD-L1 inhibitor in combination with a JAK2 inhibitor. This document also provides methods and materials involved in treating mammals having $ER^-/PgR^-/HER2^-$ cancer (e.g., $ER^-/PgR^-/HER2^-$ breast cancer) by administering a PD-1 inhibitor and/or PD-L1 inhibitor in combination with a JAK2 inhibitor.

2. Background Information

Breast cancer is a cancer that develops from breast tissue and is the most common invasive cancer in women. Breast cancer is usually treated with surgery, which may be followed by chemotherapy or radiation therapy, or both chemotherapy and radiation therapy.

SUMMARY

This document provides methods and materials involved in assessing cancer (e.g., breast cancer). For example, this document provides methods and materials for determining whether or not a cancer patient (e.g., a breast cancer patient) having $ER^-/PgR^-/HER2^-$ cancer cells is likely to have a favorable or unfavorable outcome. As described herein, cancer patients having $ER^-/PgR^-/HER2^-$ cancer (e.g., breast cancer) can be assessed to determine whether or not the cancer cells have a nucleic acid amplification at a 9p24.1 location that includes nucleic acid encoding the programmed death-ligand 1 (PD-L1), programmed death-ligand 2 (PD-L2), and Janus kinase 2 (JAK2) polypeptides. Cancer patients with cancer cells having a PD-L1/PD-L2/JAK2 amplification can be classified as being likely to have an unfavorable outcome such as cancer relapse or reoccurrence within five years of initial diagnosis or a survival time of less than five years, while cancer patients with cancer cells lacking a PD-L1/PD-L2/JAK2 amplification can be classified as being likely to have a favorable outcome such as no cancer relapse or reoccurrence within five years of initial diagnosis or a survival time of greater than five years.

This document also provides methods and materials for determining whether or not a cancer patient (e.g., a breast cancer patient) having $ER^-/PgR^-/HER2^-$ cancer cells is likely to respond to a cancer treatment that includes a PD-1 inhibitor and/or PD-L1 inhibitor in combination with a JAK2 inhibitor. As described herein, cancer patients with cancer cells having a PD-L1/PD-L2/JAK2 amplification can be classified as being likely to respond to a cancer treatment that includes a PD-1 inhibitor and/or PD-L1 inhibitor in combination with a JAK2 inhibitor.

In addition, this document provides methods and materials for treating a cancer patient (e.g., a breast cancer patient) having $ER^-/PgR^-/HER2^-$ cancer cells by administering a cancer treatment that includes a PD-1 inhibitor and/or PD-L1 inhibitor in combination with a JAK2 inhibitor. As described herein, cancer patients with $ER^-/PgR^-/HER2^-$ cancer cells having a PD-L1/PD-L2/JAK2 amplification can be treated with a cancer treatment that includes a PD-1 inhibitor and/or PD-L1 inhibitor in combination with a JAK2 inhibitor. In some cases, a cancer treatment method can include detecting the presence of cancer cells containing a PD-L1/PD-L2/JAK2 amplification prior to initiating a cancer treatment that includes a PD-1 inhibitor and/or PD-L1 inhibitor in combination with a JAK2 inhibitor.

Having the ability to identify cancer patients that are likely to have a favorable or unfavorable outcome and/or that are likely to respond to a cancer treatment that includes a PD-1 inhibitor and/or PD-L1 inhibitor in combination with a JAK2 inhibitor can allow doctors and patients to proceed with appropriate treatment options. For example, a patient identified as having $ER^-/PgR^-/HER2^-$ cancer cells containing a PD-L1/PD-L2/JAK2 amplification can be treated with a PD-1 inhibitor and/or PD-L1 inhibitor in combination with a JAK2 inhibitor.

In general, one aspect of this document features a method for identifying a mammal having cancer as being likely to have a favorable outcome. The method comprises, or consists essentially of, (a) detecting the absence of a PD-L1/PD-L2/JAK2 amplification in cancer cells obtained from the patient, and (b) classifying the patient as being likely to have a favorable outcome based at least in part on the absence. The mammal can be a human. The cancer can be $ER^-/PgR^-/HER2^-$ breast cancer, glioblastoma, or colorectal carcinoma. The favorable outcome can be no cancer relapse or reoccurrence within five years of initial diagnosis. The favorable outcome can be a survival time of greater than five years.

In another aspect, this document features a method for identifying a mammal having cancer as being likely to have an unfavorable outcome. The method comprises, or consists essentially of, (a) detecting the presence of a PD-L1/PD-L2/JAK2 amplification in cancer cells obtained from the patient, and (b) classifying the patient as being likely to have an unfavorable outcome based at least in part on the presence. The mammal can be a human. The cancer can be $ER^-/PgR^-/HER2^-$ breast cancer, glioblastoma, or colorectal carcinoma. The unfavorable outcome can be cancer relapse or reoccurrence within five years of initial diagnosis. The unfavorable outcome can be a survival time of less than five years.

In another aspect, this document features a method for treating a mammal having cancer. The method comprises, or consists essentially of, (a) administering a PD-1 inhibitor or PD-L1 inhibitor to the mammal, and (b) administering a JAK2 inhibitor to the mammal. The mammal can be a human. The cancer can be $ER^-/PgR^-/HER2^-$ breast cancer, glioblastoma, or colorectal carcinoma. The method can comprise administering the PD-1 inhibitor to the mammal. The PD-1 inhibitor can be pembrolizumab, nivolumab, MEDI0680 (AMP-514), or CT-011 (pidilizumab). The method can comprise administering the PD-L1 inhibitor to the mammal. The PD-L1 inhibitor can be MPDL3280A, MSB0010718C, MEDI4736, or BMS-936559. The JAK2 inhibitor can be ruxolitinib or pacritinib. The method can comprise detecting the presence of a PD-L1/PD-L2/JAK2 amplification in cancer cells obtained from the mammal.

In another aspect, this document features a method for identifying a mammal having cancer as being likely to have an unfavorable outcome. The method comprises, or consists essentially of, (a) detecting the presence of a PD-L1 amplification, a PD-L2 amplification, or a JAK2 amplification in cancer cells obtained from the mammal, and (b) classifying the mammal as being likely to have an unfavorable outcome based at least in part on the presence. The mammal can be a human. The cancer can be $ER^-/PgR^-/HER2^-$ breast cancer, glioblastoma, or colorectal carcinoma. The unfavorable outcome can be cancer relapse or reoccurrence within five years of initial diagnosis. The unfavorable outcome can be a survival time of less than five years.

In another aspect, this document features a method for treating a mammal having cancer. The method comprises, or consists essentially of, (a) detecting the presence of a PD-L1 amplification, a PD-L2 amplification, or a JAK2 amplification in cancer cells obtained from the mammal, (b) administering a PD-1 inhibitor or PD-L1 inhibitor to the mammal, and (c) administering a JAK2 inhibitor to the mammal. The mammal can be a human. The cancer can be $ER^-/PgR^-/HER2^-$ breast cancer, glioblastoma, or colorectal carcinoma. The method can comprise administering the PD-1 inhibitor to the mammal. The PD-1 inhibitor can be pembrolizumab, nivolumab, MEDI0680 (AMP-514), or CT-011 (pidilizumab). The method can comprise administering the PD-L1 inhibitor to the mammal. The PD-L1 inhibitor can be MPDL3280A, MSB0010718C, MEDI4736, or BMS-936559. The JAK2 inhibitor can be ruxolitinib or pacritinib.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

D) Gene expression of JAK2, PD-L1, and PD-L2 in TNBC. Quantitative Real-Time PCR was performed using the standard curve method. Target gene expression levels were normalized to the geometric mean of two reference genes (TFRC and MRPL19) selected as effectively normalizing FFPE tissue derived RNA, and normalized to a pool of RNAs prepared from a normal and from three FFPE breast tumors (TNBC, $ER^+$, and $HER2^+$). Comparisons and correlations between the expression levels of PD-L1, PD-L2, and JAK2 genes and copy number status of chromosome 9p24.1 were performed using an unpaired t test and variation among and between groups were calculated using an ANOVA test (GraphPad Prism 6).

Figure 3A:
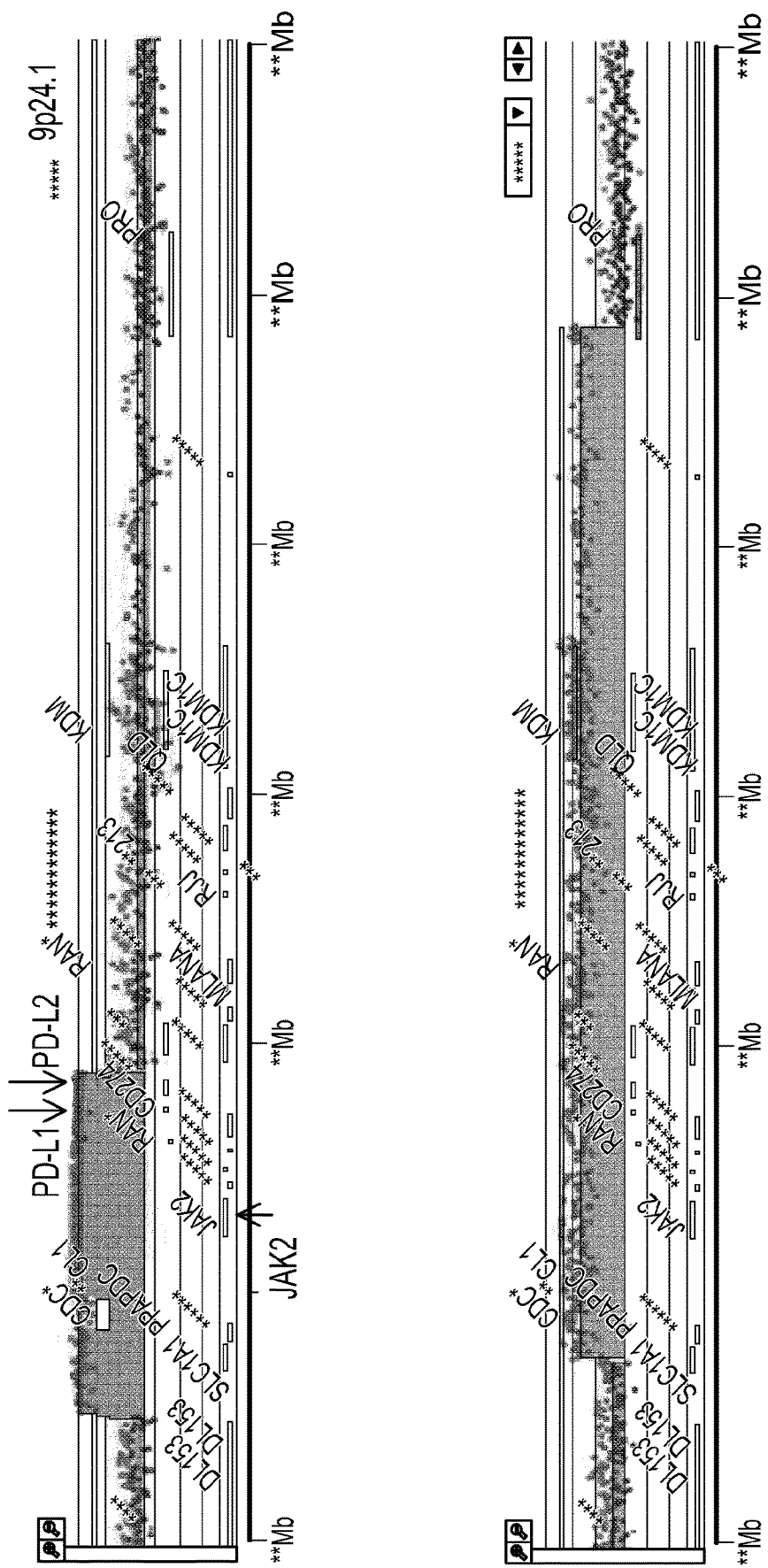
Figure 3B:
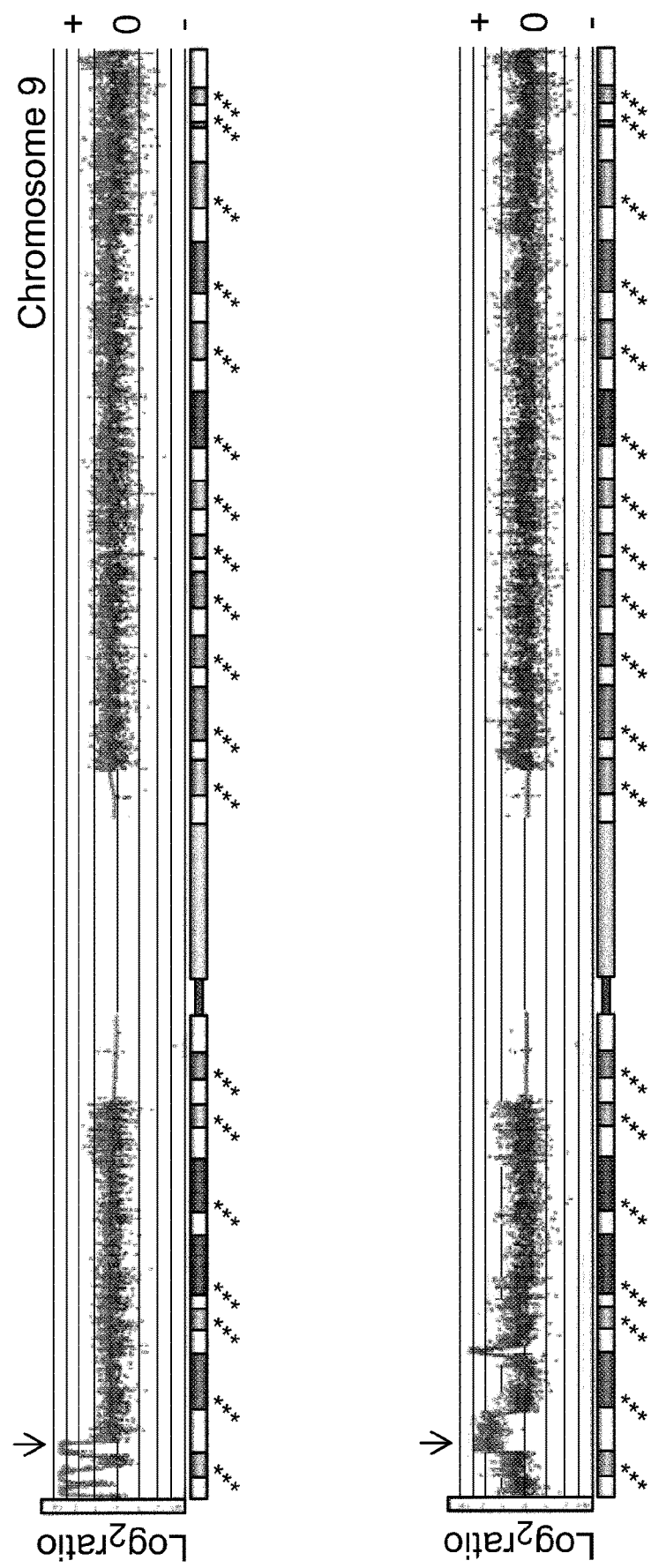

FIG. 3. Mapping the shortest region of overlap (SRO) of the PD-L1, PD-L2, JAK2 (PDJ) amplicon. Chromosome 9 CGH plots of high level and focal 9p24.1 amplicon in colorectal (top panel A, B) and breast (bottom panel A, B) cancer genomes. Shaded areas denote ADM2 defined copy number aberrant intervals.

FIG. 4. A table summarizing PDJ amplicons in TNBC.

FIG. 5. Gene expression analysis of JAK2, and PD-L1 in 15 TNBCs without aCGH data. Target gene expression levels were normalized to the geometric mean of the two reference genes and normalized to a pool of RNAs prepared from a normal and from 3 FFPE breast tumors (TNBC, $ER^+$, and $HER2^+$). TNBC SMI585 had co-occurring elevated expression of JAK2 and PD-L1.

FIG. 6. A table summarizing comparisons of clinical correlates between patients with and without PDJ amplification.

FIG. 7. PTEN homozygous deletion in a $PDJ^+$ triple negative breast cancer genome. A) DNA content flow cytometry histogram of sorted 5.0N TNBC population from FFPE tissue. B-C) Chromosome 10 and chromosome 9 CGH plots. D) Gene specific view of PTEN homozygous deletion. Blue shaded area denotes ADM2 defined copy number aberrant region.

Figure 8A:
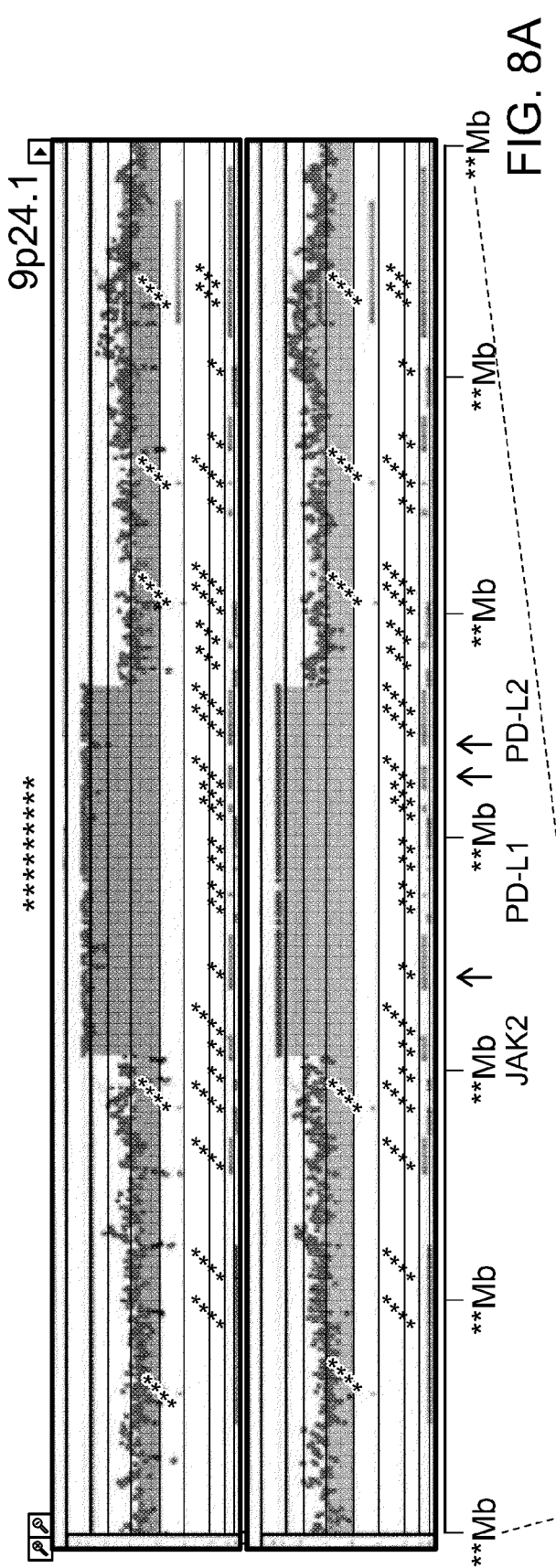
Figure 8B:
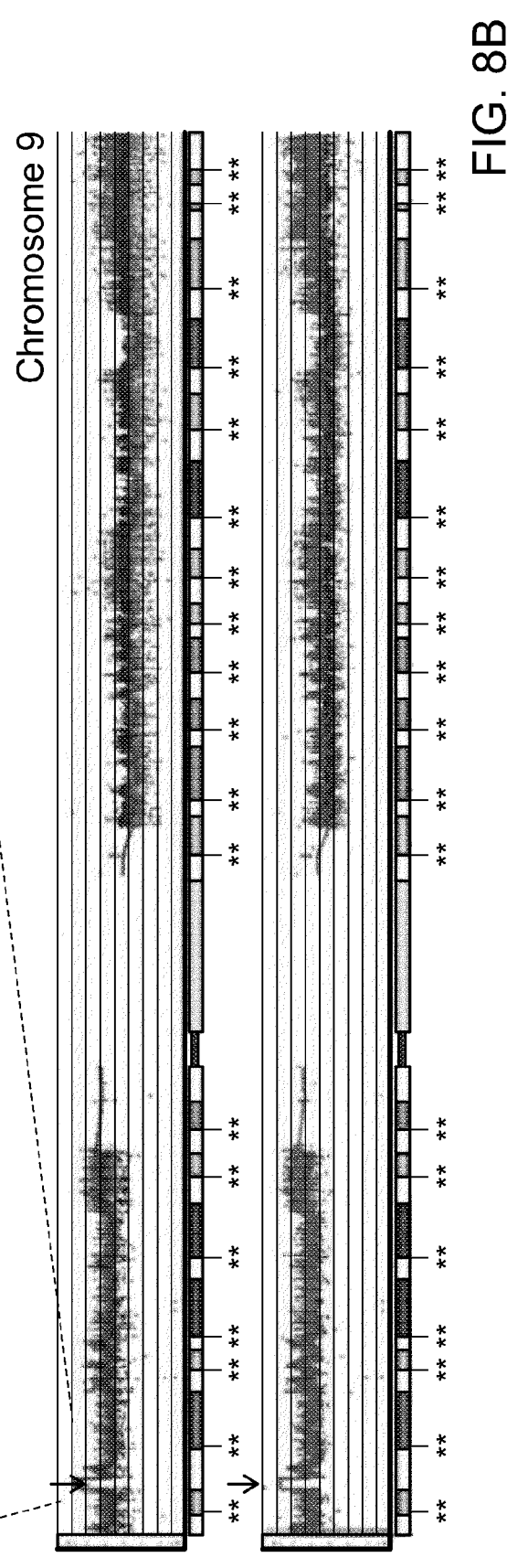
Figure 9A:
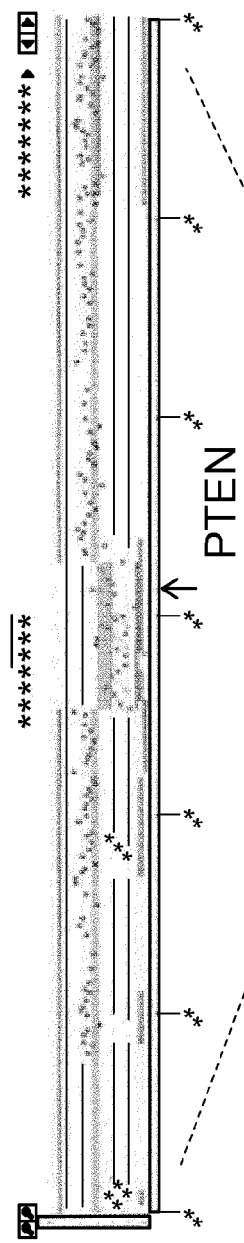
Figure 9B:
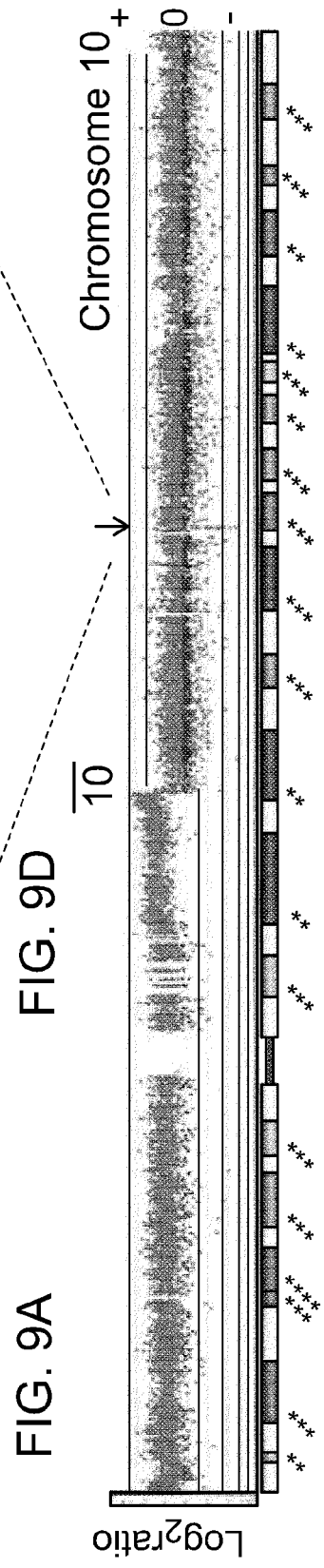
Figure 9C:
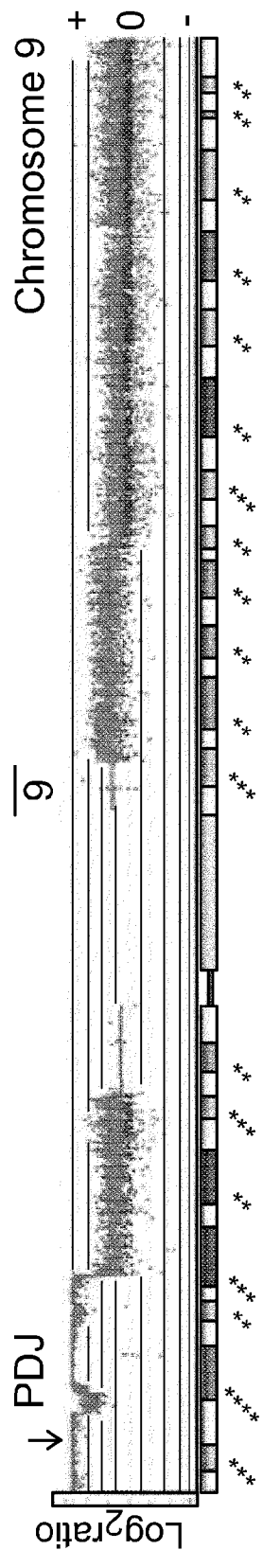
Figure 9D:
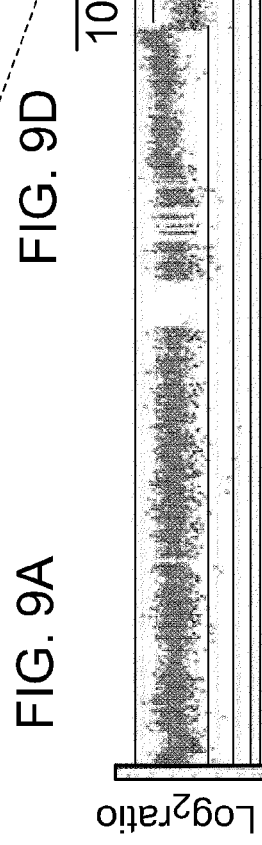

FIG. 8. PDJ amplicon present in primary colorectal carcinoma and a matching lymph node biopsy. A) Gene specific view of shared 9p24.1 amplicon in primary (top) and lymph node (bottom). B) Chromosome 9 CGH plots of primary (top) and lymph node (bottom). Blue and red shaded area denotes ADM2 defined copy number aberrant region.

FIG. 9. PTEN deletion in a $PDJ^+$ triple negative breast cancer genome. A) DNA content flow cytometry histogram of sorted 3.9N TNBC population from FFPE tissue. B-C) Chromosome 10 and chromosome 9 CGH plots. D) Gene specific view of PTEN deletion. Blue shaded area denotes ADM2 defined copy number aberrant region.

Figure 10A:
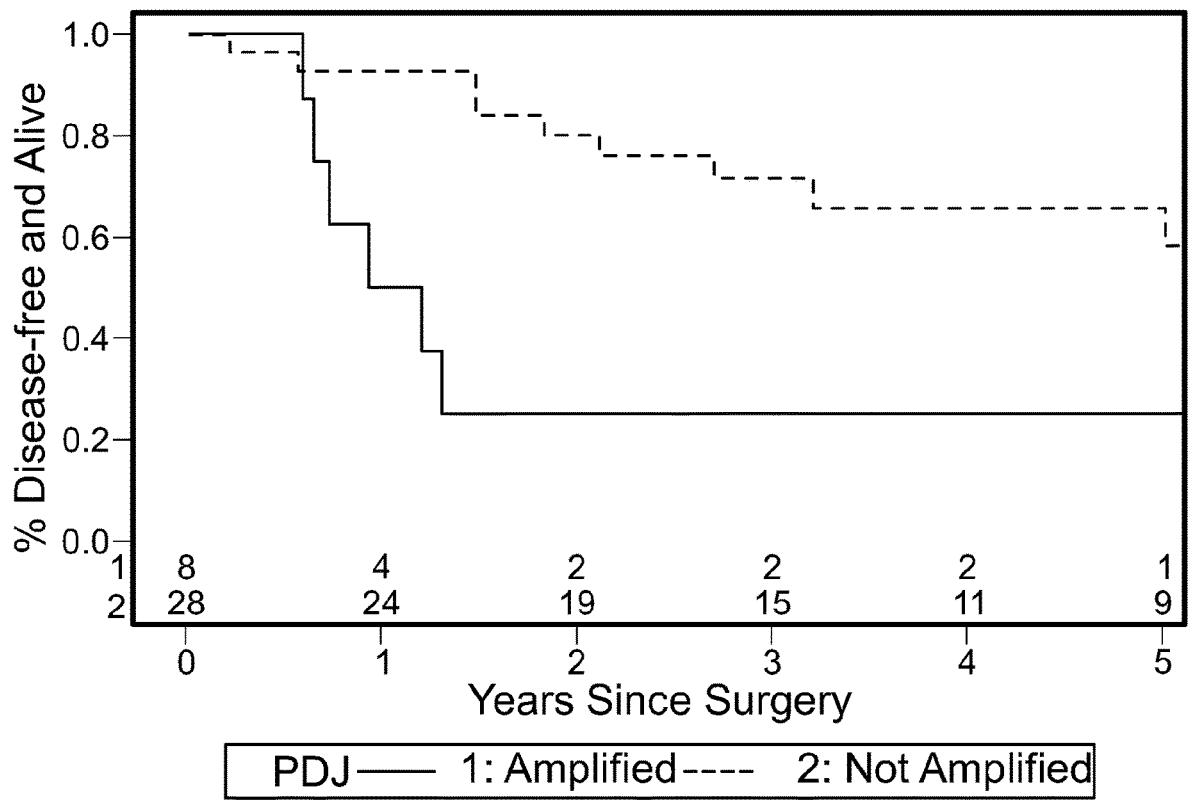
Figure 10B:
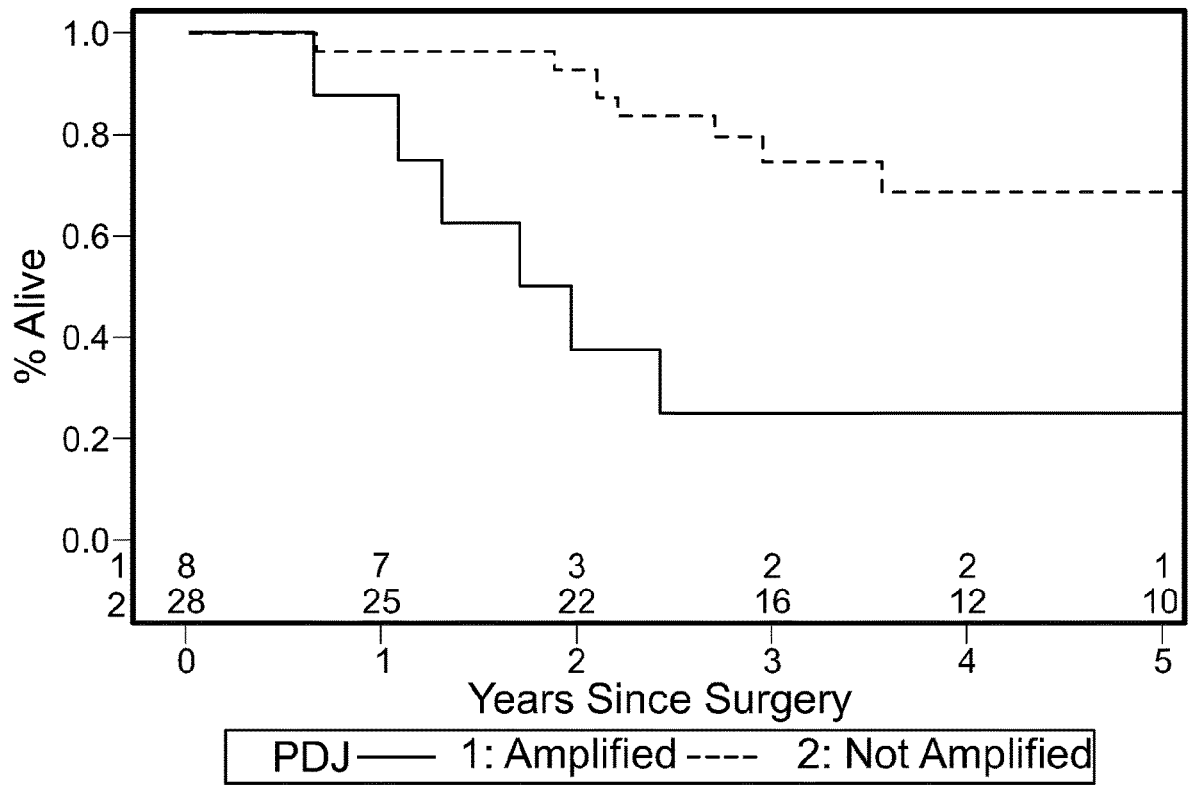

FIG. 10. Clinical outcomes for TNBC patients with or without PDJ amplicon. A) Progression free survival. Lower disease-free survival at 5 years 25.0% vs. 66.0%, p=0.005. B) Overall survival. Lower overall survival at 5 years 25.0% vs. 69.0%, p=0.004. Median follow up is 4.7 years (range 0.9-12.0 years).

DETAILED DESCRIPTION

This document provides methods and materials involved in assessing cancer (e.g., breast cancer, glioblastoma, colorectal carcinoma, prostate carcinoma, bladder carcinoma, or primary or metastatic cancers arising in solid or hematopoetic tissues). For example, this document provides methods and materials for determining whether or not a mammal having cancer (e.g., $ER^-/PgR^-/HER2^-$ breast cancer, glioblastoma, colorectal carcinoma, bladder carcinoma, renal cell carcinoma, or lymphoma) is likely to have a favorable or unfavorable outcome. Any appropriate mammal having cancer can be assessed as described herein. For example, humans, dogs, cats, horses, cattle, pigs, sheep, goats, monkeys, apes, hamsters, rats, and mice can be assessed.

As described herein, cancer patients having cancer (e.g., ER⁻/PgR⁻/HER2⁻ breast cancer) can be assessed to determine whether or not the cancer cells have a nucleic acid amplification at a 9p24.1 location that includes nucleic acid encoding the PD-L1, PD-L2, and JAK2 polypeptides. Cancer patients with cancer cells having a PD-L1/PD-L2/JAK2 amplification can be classified as being likely to have an unfavorable outcome. An unfavorable outcome can be cancer relapse or reoccurrence within five years (e.g., within one, two, three, four, or five years) of initial diagnosis. In some cases, an unfavorable outcome can be a survival time of less than five years (e.g., less than one, two, three, four, or five years). Cancer patients with cancer cells lacking a PD-L1/PD-L2/JAK2 amplification can be classified as being likely to have a favorable outcome. A favorable outcome can be no cancer relapse or reoccurrence within five years or longer (e.g., six, seven, eight, nine, ten, or more years) of initial diagnosis. In some cases, a favorable outcome can be a survival time of greater than five years (e.g., six, seven, eight, nine, ten, or more years).

In some cases, cancer patients having cancer (e.g., ER⁻/PgR⁻/HER2⁻ breast cancer) can be assessed to determine whether or not the cancer cells have a nucleic acid amplification at a 9p24.1 location that includes nucleic acid encoding a PD-L1 polypeptide, a PD-L2 polypeptide, or a JAK2 polypeptide. In some cases, cancer patients having cancer (e.g., ER⁻/PgR⁻/HER2⁻ breast cancer) can be assessed to determine whether or not the cancer cells have a nucleic acid amplification at a 9p24.1 location that includes nucleic acid encoding a combination of a PD-L1 polypeptide, a PD-L2 polypeptide, and a JAK2 polypeptide (e.g., an amplification of nucleic acid encoding a PD-L1 polypeptide and a PD-L2 polypeptide, or an amplification of nucleic acid encoding a JAK2 polypeptide and a PD-L1 polypeptide). Cancer patients with cancer cells having a PD-L1 amplification, a PD-L2 amplification, or a JAK2 amplification (or combinations thereof) can be classified as being likely to have an unfavorable outcome. An unfavorable outcome can be cancer relapse or reoccurrence within five years (e.g., within one, two, three, four, or five years) of initial diagnosis. In some cases, an unfavorable outcome can be a survival time of less than five years (e.g., less than one, two, three, four, or five years). Cancer patients with cancer cells lacking a PD-L1 amplification, a PD-L2 amplification, and a JAK2 amplification can be classified as being likely to have a favorable outcome. A favorable outcome can be no cancer relapse or reoccurrence within five years or longer (e.g., six, seven, eight, nine, ten, or more years) of initial diagnosis. In some cases, a favorable outcome can be a survival time of greater than five years (e.g., six, seven, eight, nine, ten, or more years).

In some cases, cancer patients having cancer (e.g., ER⁻/PgR⁻/HER2⁻ breast cancer) can be assessed to determine whether or not the cancer cells have a nucleic acid amplification at a 9p24.1 location that results in an increased level of mRNA encoding a PD-L1 polypeptide, a PD-L2 polypeptide, and/or a JAK2 polypeptide. Cancer patients with cancer cells having a PD-L1 amplification, a PD-L2 amplification, and/or a JAK2 amplification that results in an increased level of mRNA encoding a PD-L1 polypeptide, a PD-L2 polypeptide, and/or a JAK2 polypeptide can be classified as being likely to have an unfavorable outcome. An unfavorable outcome can be cancer relapse or reoccurrence within five years (e.g., within one, two, three, four, or five years) of initial diagnosis. In some cases, an unfavorable outcome can be a survival time of less than five years (e.g., less than one, two, three, four, or five years). Cancer patients with cancer cells lacking a PD-L1 amplification, a PD-L2 amplification, and a JAK2 amplification that results in an increased level of mRNA encoding a PD-L1 polypeptide, a PD-L2 polypeptide, and a JAK2 polypeptide can be classified as being likely to have a favorable outcome. A favorable outcome can be no cancer relapse or reoccurrence within five years or longer (e.g., six, seven, eight, nine, ten, or more years) of initial diagnosis. In some cases, a favorable outcome can be a survival time of greater than five years (e.g., six, seven, eight, nine, ten, or more years).

This document also provides methods and materials for determining whether or not a mammal (e.g., a human) having cancer (e.g., ER⁻/PgR⁻/HER2⁻ breast cancer, glioblastoma, colorectal carcinoma, bladder carcinoma, renal cell carcinoma, or lymphoma) is likely to respond to a cancer treatment that includes a PD-1 inhibitor and/or a PD-L1 inhibitor in combination with a JAK2 inhibitor. As described herein, mammals (e.g., humans) with cancer cells having a PD-L1/PD-L2/JAK2 amplification can be classified as being likely to respond to a cancer treatment that includes a PD-1 inhibitor and/or PD-L1 inhibitor in combination with a JAK2 inhibitor. In some cases, mammals (e.g., humans) with cancer cells having a PD-L1 amplification, a PD-L2 amplification, or a JAK2 amplification (or combinations thereof) can be classified as being likely to respond to a cancer treatment that includes a PD-1 inhibitor and/or PD-L1 inhibitor in combination with a JAK2 inhibitor.

Any appropriate method can be used to determine whether or not cancer cells from a mammal have a PD-L1/PD-L2/JAK2 amplification, or a PD-L1 amplification, or a PD-L2 amplification, or a JAK2 amplification (or a combination thereof). For example, Southern blot techniques, PCR-based techniques, fluorescence in situ hybridization (FISH) techniques, or sequencing techniques can be used to detect the presence or absence of a PD-L1/PD-L2/JAK2 amplification. For example, a FISH technique can be designed to use centromere specific probes such as Vysis CEP3 (Spectrum Red) and Vysis CEP7 (Spectrum Green) (Vysis Inc., Abbott Laboratories, Downers Grove, Ill.) to determine centromere copy numbers. For PD-L1 and JAK2 gene copy analysis, FISH probes mapped to chromosome 9p24.1-ptel (http://genome.ucsc.edu/cgi-bin/hgTracks?db=hg19&position=chr9%3A1-7293900&hgsid=418127357_EATu0e1D1kthxmtWC3SmnkeHoWie) and the Vysis CEP9 (Spectrum Green) can be used. Before hybridization, slides can be treated, for example, according to the Paraffin Pretreatment Reagent Kit protocol (Vysis). Hybridization and post-hybridization washes can be performed, and images can be obtained using a Zeiss Axioplan 2 or similar fluorescence microscope (Zeiss, Feldbach, Switzerland) equipped with an ISIS-digital or equivalent camera (MetaSystems, Altlussheim, Germany). FISH images can be acquired with a 100× objective (Plan-Apochromat, Zeiss), and the samples can be assessed for the presence or absence of a PD-L1/PD-L2/JAK2 amplification.

In addition, this document provides methods and materials for treating cancer (e.g., ER⁻/PgR⁻/HER2⁻ breast cancer, glioblastoma, colorectal carcinoma, bladder carcinoma, renal cell carcinoma, or lymphoma) by administering a cancer treatment that includes a PD-1 inhibitor and/or PD-L1 inhibitor in combination with a JAK2 inhibitor. For example, a mammal having cancer (e.g., ER⁻/PgR⁻/HER2⁻ breast cancer, glioblastoma, colorectal carcinoma, bladder carcinoma, renal cell carcinoma, or lymphoma) where the cancer cells have a PD-L1/PD-L2/JAK2 amplification (or a PD-L1 amplification, a PD-L2 amplification, a JAK2 amplification, or a combination thereof) can be treated with a cancer treatment that includes a PD-1 inhibitor and/or PD-L1 inhibitor in combination with a JAK2 inhibitor. In some cases, a cancer treatment method provided herein can include detecting the presence of cancer cells containing a PD-L1/PD-L2/JAK2 amplification (or a PD-L1 amplification, a PD-L2 amplification, a JAK2 amplification, or a combination thereof) prior to initiating a cancer treatment that includes a PD-1 inhibitor and/or PD-L1 inhibitor in combination with a JAK2 inhibitor.

Any appropriate mammal having cancer cells containing a PD-L1/PD-L2/JAK2 amplification (or a PD-L1 amplification, a PD-L2 amplification, a JAK2 amplification, or a combination thereof) can be treated as described herein. For example, humans and other primates such as monkeys having cancer cells containing a PD-L1/PD-L2/JAK2 amplification (or a PD-L1 amplification, a PD-L2 amplification, a JAK2 amplification, or a combination thereof) can be treated with one or more (e.g., one, two, three, four, or more) PD-1 inhibitors and/or one or more (e.g., one, two, three, four, or more) PD-L1 inhibitors in combination with one or more (e.g., one, two, three, four, or more) JAK2 inhibitors. In some cases, dogs, cats, horses, cows, pigs, sheep, mice, and rats can be treated with one or more PD-1 inhibitors and/or one or more PD-L1 inhibitors in combination with one or more JAK2 inhibitors as described herein.

Once identified as having cancer cells containing a PD-L1/PD-L2/JAK2 amplification (or a PD-L1 amplification, a PD-L2 amplification, a JAK2 amplification, or a combination thereof), the mammal can be administered one or more PD-1 inhibitors and/or one or more PD-L1 inhibitors in combination with one or more JAK2 inhibitors. Examples of PD-1 inhibitors include, without limitation, pembrolizumab, nivolumab, MEDI0680 (AMP-514), and CT-011 (pidilizumab). Examples of PD-L1 inhibitors include, without limitation, MPDL3280A, MSB0010718C, MEDI4736, and BMS-936559. Examples of JAK2 inhibitors include, without limitation, ruxolitinib and pacritinib. In some cases, one or more PD-L2 inhibitors can be used in addition to or in place of PD-1 inhibitors and/or PD-L1 inhibitors. For example, the mammal can be administered one or more PD-L2 inhibitors in combination with one or more JAK2 inhibitors. An example of a PD-L2 inhibitor includes, without limitation, AMP-224.

In some cases, one or more PD-1 inhibitors, one or more PD-L1 inhibitors, one or more PD-L2 inhibitors, and/or one or more JAK2 inhibitors can be formulated into one or more pharmaceutically acceptable compositions for administration to a mammal having cancer (e.g., cancer with cancer cells containing a PD-L1/PD-L2/JAK2 amplification (or a PD-L1 amplification, a PD-L2 amplification, a JAK2 amplification, or a combination thereof)). For example, a therapeutically effective amount of a PD-1 inhibitor can be formulated together with a JAK2 inhibitor and one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

A pharmaceutical composition containing one or more PD-1 inhibitors, one or more PD-L1 inhibitors, one or more PD-L2 inhibitors, and/or one or more JAK2 inhibitors can be designed for oral or parenteral (including subcutaneous, intramuscular, intravenous, and intradermal) administration. When being administered orally, a pharmaceutical composition containing one or more PD-1 inhibitors, one or more PD-L1 inhibitors, one or more PD-L2 inhibitors, and/or one or more JAK2 inhibitors can be in the form of a pill, tablet, or capsule. Compositions suitable for parenteral administration include aqueous and non-aqueous sterile injection solutions that can contain anti-oxidants, buffers, bacteriostats, and solutes which render the formulation isotonic with the blood of the intended recipient; and aqueous and non-aqueous sterile suspensions which may include suspending agents and thickening agents. The formulations can be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules, and tablets.

Such injection solutions can be in the form, for example, of a sterile injectable aqueous or oleaginous suspension. This suspension may be formulated using, for example, suitable dispersing or wetting agents (such as, for example, Tween 80) and suspending agents. The sterile injectable preparation can be a sterile injectable solution or suspension in a non-toxic parenterally-acceptable diluent or solvent, for example, as a solution in 1,3-butanediol. Examples of acceptable vehicles and solvents that can be used include, without limitation, mannitol, water, Ringer's solution, and isotonic sodium chloride solution. In addition, sterile, fixed oils can be used as a solvent or suspending medium. In some cases, a bland fixed oil can be used such as synthetic mono- or di-glycerides. Fatty acids, such as oleic acid and its glyceride derivatives can be used in the preparation of injectables, as can natural pharmaceutically-acceptable oils, such as olive oil or castor oil, including those in their polyoxyethylated versions. In some cases, these oil solutions or suspensions can contain a long-chain alcohol diluent or dispersant.

In some cases, a pharmaceutically acceptable composition including one or more PD-1 inhibitors, one or more PD-L1 inhibitors, one or more PD-L2 inhibitors, and/or one or more JAK2 inhibitors can be administered locally or systemically. For example, a composition containing a JAK2 inhibitor can be administered locally by injection into lesions at surgery or by subcutaneous administration of a sustained release formulation. In some cases, a composition containing one or more PD-1 inhibitors, one or more PD-L1 inhibitors, one or more PD-L2 inhibitors, and/or one or more JAK2 inhibitors can be administered systemically, orally or by injection to a mammal (e.g., a human).

Effective doses can vary depending on the severity of the cancer, the route of administration, the age and general health condition of the subject, excipient usage, the possibility of co-usage with other therapeutic treatments such as use of chemotherapeutic agents, and the judgment of the treating physician. Examples of chemotherapeutic agents that can be used in combination with one or more PD-1 inhibitors, one or more PD-L1 inhibitors, one or more PD-L2 inhibitors, and/or one or more JAK2 inhibitors include, without limitation, taxane therapies, anthracycline therapies, gemcitabine therapies, and other chemotherapies. Examples of taxane therapies include, without limitation, cancer treatments that involve administering taxane agents such as paclitaxel, nanoparticle albumin bound paclitaxel (nab-paclitaxel), docetaxel, or other microtubule disrupting agents such as vinblastine, vincristine, or vinorelbine. In some cases, drugs used to treat gout or chochicine can be used as a mitotic inhibitor to treat a mammal having cancer. Examples of anthracycline therapies include, without limitation, cancer treatments that involve administering anthracycline agents such as doxorubicin, liposomal doxorubicin, and epirubicin. Other chemotherapeutics that can be used clinically in breast cancer include, without limitation, cyclophosphamide, 5-fluorouracil, capecitabine, ixabepilone, erubilin, palbociclib, and methotrexate.

An effective amount of a composition containing one or more PD-1 inhibitors, one or more PD-L1 inhibitors, one or more PD-L2 inhibitors, and/or one or more JAK2 inhibitors can be any amount that results in clinically relevant efficacy of the condition being treated (e.g. cancer). If a particular mammal fails to respond to a particular amount, then the amount of inhibitor (e.g., PD-1 inhibitor, PD-L1 inhibitor, PD-L2 inhibitor, and/or JAK2 inhibitor) can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration can be any frequency that reduces the severity of a symptom of a condition to be treated (e.g., cancer). For example, the frequency of administration can be from about once a week to about three times a day, or from about twice a month to about six times a day, or from about twice a week to about once a day. The frequency of administration can remain constant or can be variable during the duration of treatment. A course of treatment with a composition containing one or more PD-1 inhibitors, one or more PD-L1 inhibitors, one or more PD-L2 inhibitors, and/or one or more JAK2 inhibitors can include rest periods. For example, a composition containing one or more PD-1 inhibitors, one or more PD-L1 inhibitors, one or more PD-L2 inhibitors, and/or one or more JAK2 inhibitors can be administered daily over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing one or more PD-1 inhibitors, one or more PD-L1 inhibitors, one or more PD-L2 inhibitors, and/or one or more JAK2 inhibitors can be any duration that reduces the severity of a symptom of the condition to be treated (e.g., cancer). Thus, the effective duration can vary from several days to several weeks, months, or years. In general, the effective duration for the treatment of cancer can range in duration from six months to one year. Multiple factors can influence the actual effective duration used for a particular treatment. For example, an effective duration can vary with the frequency of administration, effective amount, use of multiple treatment agents, route of administration, and severity of the condition being treated.

The invention will be further described in the following examples, which do not limit the scope of the invention described in the claims.

EXAMPLES

Example 1—High-Level Amplification of Chromosome 9p24 Targeting PD-L1 and JAK2 Correlates with Worse Disease Free Survival and Overall Survival in Triple Negative Breast Cancer Clinical Samples Triple negative breast cancer (TNBC) is a subgroup of breast tumors that does not express clinically significant levels of the estrogen receptor (ER), progesterone receptor (PgR), and HER2. TNBC, ER$^+$, and HER2$^-$ samples were obtained. Tumor specimens were obtained from formalin fixed paraffin embedded (FFPE) archived breast cancer samples obtained at the time of definitive surgical resection. All breast cancers underwent pathologic review and were evaluated by immunohistochemistry for ER and PgR, and by immunohistochemistry with or without FISH for Her2/neu under CLIA/CAP guidelines. TNBC samples were also obtained from The Inflammatory Breast Cancer Research Foundation (IBCRF) Biobank. Additional flow sorted TNBC data was obtained from a previous study of breast cancer genomes (Przybytkowski et al., *BMC Genomics*, 15:579 (2014)). PDA, glioblastoma, and colon samples also were obtained.

FFPE Sample Preparation

Prior to sorting, excess paraffin was removed with a scalpel from either side of 40-60 µm scrolls then processed as described elsewhere (Holley et al., *PLoS One*, 7:e50586 (2012)). Briefly, each sectioned piece was collected into individual microcentrifuge tubes then washed three times with 1 mL Xylene for 5 minutes to remove remaining paraffin. Each sample was rehydrated in sequential ethanol washes (100% 5 minutes×2, then 95%, 70%, 50% and 30% ethanol) and washed 2 times in 1 mL 1 mM EDTA pH 8.0. A 1 mL aliquot of 1 mM EDTA pH 8.0 was added to the samples and incubated at 95° C. for 80 minutes to facilitate the removal of protein cross-links present in FFPE tissue. Samples were then cooled to room temperature for >5 minutes, followed by addition of 300 µL PBS pH 7.4 and gentle centrifugation for 2 minutes at 3.6×g. The supernatant was carefully removed, and the pellet washed three times with 1 mL PBS pH 7.4/0.5 mM CaCl$_2$ to remove EDTA. Each sample was digested overnight (6-17 hours) in 1 mL of a freshly prepared enzymatic cocktail containing 50 units/mL of collagenase type 3, 80 units/mL of purified collagenase, and 100 units/mL of hyaluronidase in PBS pH 7.4/0.5 mM CaCl$_2$ buffer. Following overnight digestion 500 L NST buffer (146 mM NaCl, 10 mM Tris-HCl, pH 7.5, 1 mM CaCl$_2$, 0.5 mM MgSO$_4$, 21 mM MgCl$_2$, 0.05% bovine serum albumin, 0.2% Nonidet P40 (Sigma)) with 4,6-diamindino-2-phenylindole (DAPI; 10 µg/mL) was added to each sample to facilitate pelleting. Samples were centrifuged for 5 minutes at 3000×g, after which pellets were resuspended in 750 µL of NST/10% fetal bovine serum and then passed through a 25 G needle 10-20 times. A single 50 µm scroll was used from each FFPE tissue block to obtain sufficient numbers of intact nuclei for subsequent sorting and molecular assays.

Flow Cytometry

Biopsies were minced in the presence of NST buffer and DAPI as described elsewhere (Galipeau et al., *PLoS Med*, 4:e67 (2007); Maley et al., *Nat. Genet.*, 38:468-473 (2006); and Rabinovitch et al., *Am. J. Gastroenterol.*, 96:3071-3083 (2001)). Prior to sorting, each sample was filtered through a 35 µm mesh and collected into a 5 mL polypropylene round bottom tube. The mesh was rinsed with an additional 750 µL of NST/10% fetal bovine serum and placed on ice while processing remaining samples. The total volume in the tube for each sample was approximately 1.5 mL. An equal volume of 20 µg/mL DAPI was added to each tube to achieve a final concentration of 10 µg/mL DAPI for flow sorting with a BD Influx cytometer with ultraviolet excitation (Becton-Dickinson, San Jose, Calif.). The optimal settings for sorting FFPE samples with the Influx sorter were as follows: Drop formation was achieved with piezzo amplitude of 6-10 volts and a drop frequency of 30 khertz. The sort mode was set to purity yield with a drop delay of 31.5-32. Sheath fluid pressure was typically 17-18 psi with a 100 um nozzle.

For single parameter DNA content assays, DAPI emission was collected at >450 nm. DNA content and cell cycle were then analyzed using the software program MultiCycle (Phoenix Flow Systems, San Diego, Calif.).

DNA Extraction

DNA from sorted nuclei was extracted using an amended protocol from QIAamp® DNA Micro Kit from Qiagen (Valencia, Calif.). Briefly, each sorted sample was resuspended in 180 µL buffer ATL and 20 µL proteinase K (20 mg/mL) then incubated for 3 hours at 56° C. for complete lysis. Samples were bound and washed according to QIAamp® DNA Micro Kit instructions, eluted into 50 µL of H$_2$0, then precipitated overnight with 5 µL 3 M sodium acetate and 180 µL 100% EtOH. Each sample was then centrifuged for 30 minutes at 20,000×g, and washed in 1 mL of 70% EtOH for 30 minutes at 20,000×g. The samples were carefully decanted, and the DNA pellet was dried by speed vacuum then resuspended in a small volume (e.g., 10-50 µL) of H$_2$0 for final concentrations suitable for accurate quantitation.

aCGH Analysis

DNAs were treated with DNAse 1 prior to Klenow-based labeling. High molecular weight reference templates were digested for 30 minutes while the smaller fragmented FFPE-derived DNA samples were digested for only 1 minute. In each case, 1 µL of 10× DNase 1 reaction buffer and 2 µL of DNase 1 dilution buffer were added to 7 µL of DNA sample and incubated at room temperature then transferred to 70° C. for 30 minutes to deactivate DNase 1. Sample and reference templates were then labeled with Cy-5 dUTP and Cy-3 dUTP, respectively, using a BioPrime labeling kit (Invitrogen, Carlsbad, Calif.) as described elsewhere (Ruiz et al., *Proc. Natl. Acad. Sci. USA*, 108:12054-12059 (2011)). All labeling reactions were assessed using a Nanodrop assay (Nanodrop, Wilmington, Del.) prior to mixing and hybridization to CGH arrays (Agilent Technologies, Santa Clara, Calif.) for 40 hours in a rotating 65° C. oven. All microarray slides were scanned using an Agilent 2565C DNA scanner, and the images were analyzed with Agilent Feature Extraction version 10.7 using default settings. The aCGH data was assessed with a series of QC metrics then analyzed using an aberration detection algorithm (ADM2) (Lipson et al., *J. Comput. Biol.*, 13:215-228 (2006)). The latter identifies all aberrant intervals in a given sample with consistently high or low log ratios based on the statistical score derived from the average normalized log ratios of all probes in the genomic interval multiplied by the square root of the number of these probes. This score represents the deviation of the average of the normalized log ratios from its expected value of zero and is proportional to the height h (absolute average log ratio) of the genomic interval, and to the square root of the number of probes in the interval.

Expression Analysis

Total RNA was extracted from one whole-tissue 50 µm thick section using RNeasy FFPE RNA Isolation Kit (Qiagen). RNA quantification was performed using Qubit 2.0 fluorometer (Life Technologies) and Qubit RNA HS assay kit (molecular probes). Reverse transcription was carried out using SuperScript® VILO™ cDNA Synthesis Kit (Life Technologies) and 200 ng of RNA per reaction, with triplicate reactions performed for each sample (Piscuoglio et al., *Mol. Oncol.*, 8:1588-1602 (2014)). Each of the 31 samples produced sufficient RNA yield and quality. Quantitative Real-Time PCR was performed for CD274, PDCD1LG2, and JAK2 (Hs01125301_m1, Hs01057777_m1, Hs00234567_m1, respectively; Life Technologies) with TaqMan® chemistry on the ABI Prism 7900HT (Applied Biosystems), using the standard curve method. Two reference genes were used TFRC and MRPL19 (Hs00174609_m1 and Hs00608519_m1, respectively; Life Technologies), previously selected as effectively normalizing for degradation of the FFPE-RNA. Target gene expression levels were normalized to the geometric mean of the two reference genes and normalized to a pool of RNAs prepared from a normal and from 3 FFPE breast tumors (TNBC, ER$^+$, and HER2$^+$). All statistical comparisons and correlations between the expression levels of PD-L1, PD-L2, and JAK2 genes and copy number status of chromosome 9p24.1 were performed using an unpaired t test, and variation among and between groups were calculated using an ANOVA test (GraphPad Prism 6). The p-values <0.05 were considered significant.

Statistical Analysis

Group comparisons used two-sample t-tests for continuous variables and chi-squared tests for categorical variables. Time to recurrence was defined as the time from primary surgery to first local, regional, or distant recurrence. Overall survival analysis included all deaths as events regardless of cause. Recurrence rate and overall survival rate at 5 years were estimated using the method of Kaplan and Meier. Time to recurrence and overall survival were compared between groups using a log-rank test. Median follow-up was 4.7 years (range 0.9-12 years). P-values <0.05 were considered statistical significant throughout.

Results

Tumor samples from 326 subjects were evaluated for copy number aberrations. The tissues included triple negative breast cancer (TNBC) n=41, HER2$^+$ breast cancer n=15, ER$^+$HER2$^-$ breast cancer n=8, pancreatic adenocarcinoma n=150 (including 30 liver metastases), colorectal carcinoma n=68, and glioblastoma n=44. In order to accurately survey the genomes of these solid tissue tumors, DNA content-based flow cytometry was used to identify and purify distinct populations of diploid, tetraploid, and aneuploid populations from each tissue (Holley et al., *PLoS One*, 7:e50586 (2012); and Ruiz et al., *Proc. Natl. Acad. Sci. USA*, 108:12054-12059 (2011)). These included both fresh frozen and formalin fixed paraffin embedded (FFPE) clinical samples.

Figure 1C:
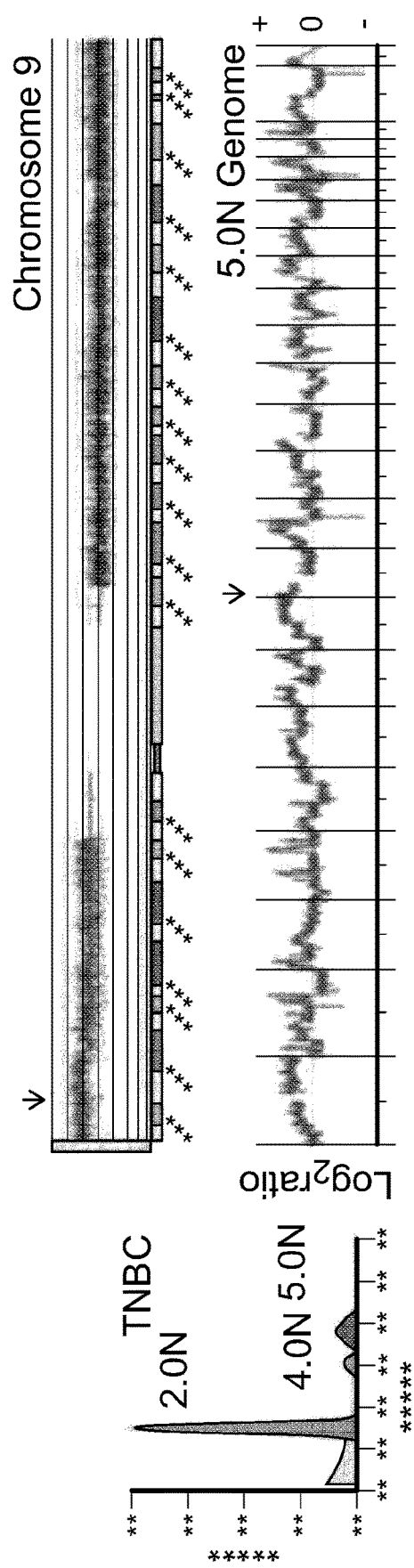
FIG. 1. DNA content flow cytometry histograms and whole genome and chromosome 9 aCGH plots of flow sorted tumor populations. A) Colorectal (CRC) and B-C) triple negative breast cancers (TNBC) with high level (log2ratio>1) 9p24.1 amplicon. Blue arrows denote PD-L1, PD-L2, JAK2 locus.
Figure 2A:
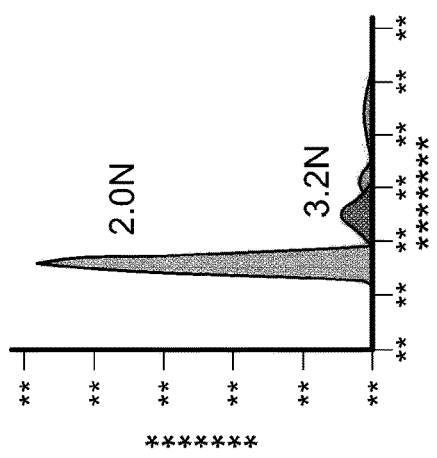
FIG. 2. The 9p24 amplicon in a triple negative breast cancer genome. A) Flow histogram of sorted 3.2N TNBC population from formalin fixed paraffin embedded (FFPE) tissue. B) Chromosome 9 CGH plot and detection of 9p24 amplicon. C) Gene specific view of amplicon. Red shaded area denotes ADM2 defined copy number aberrant region.
Figure 2B:
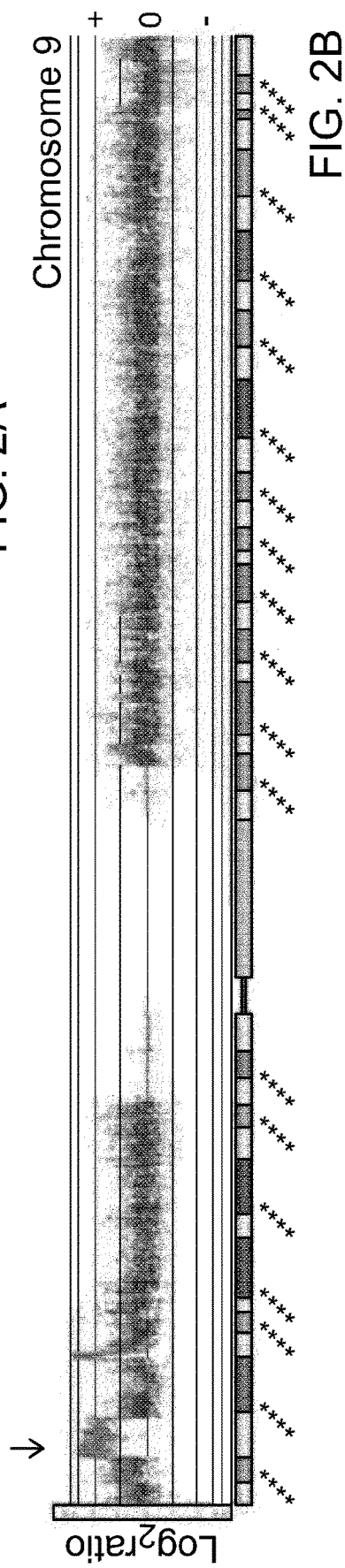
Figure 2C:
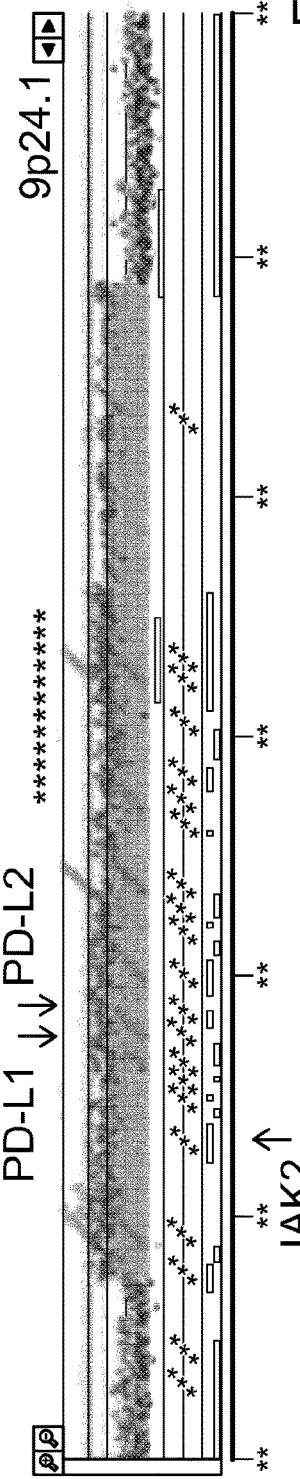
Figure 2D:
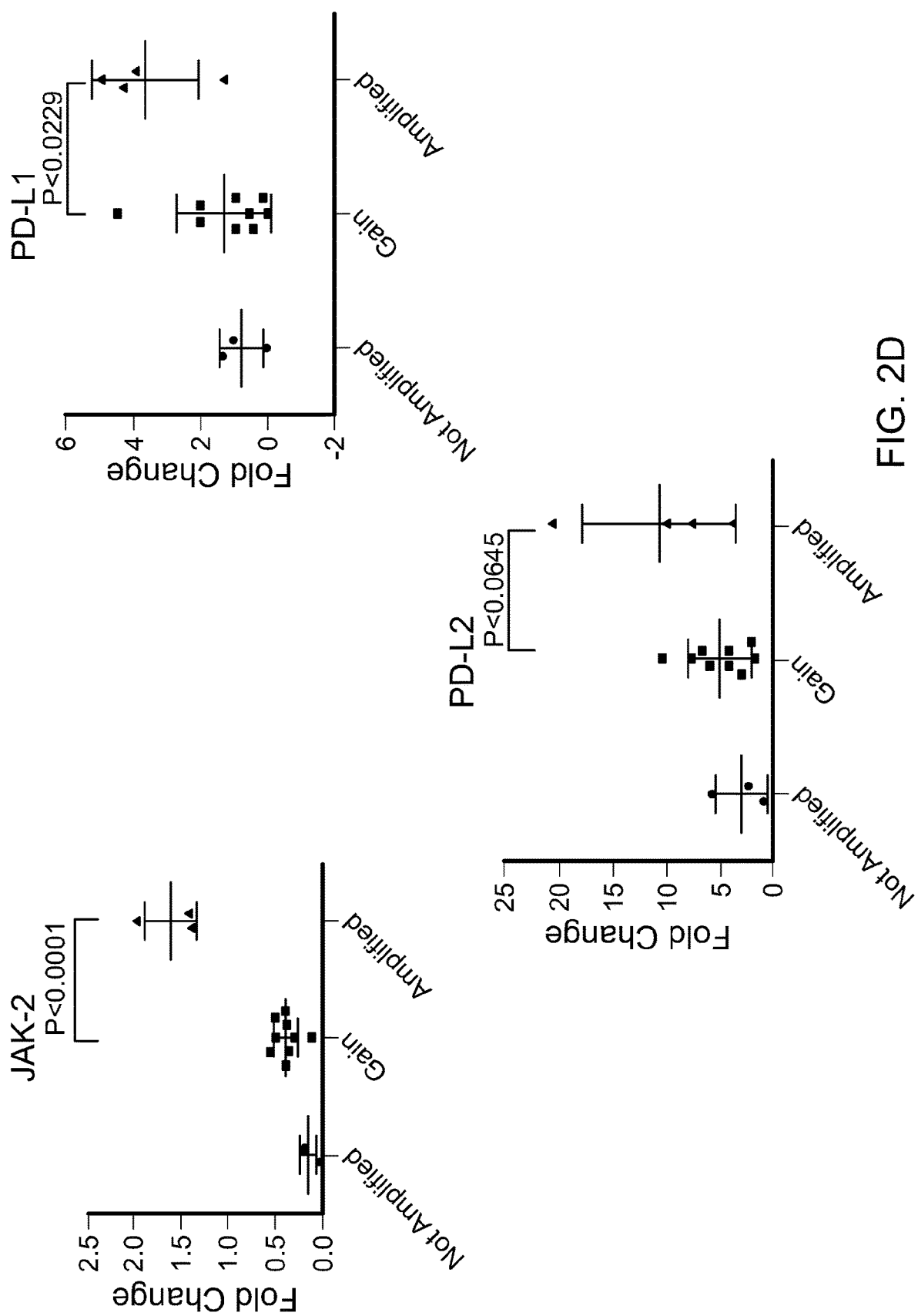

The genomes of each sorted tumor cell population were then interrogated with whole genome oligonucleotide CGH arrays. Copy number aberrant intervals were identified, and their genomic boundaries mapped using a step gram algorithm (Lipson et al., *J. Comput. Biol.*, 13:215-228 (2006)). Amplicons were then ranked within each sample based on their fold change and their overall prevalence in tumor genomes. A recurring top ranked and high level (log2ratio>1) amplicon that targeted 9p24.1 was detected in 12/41 TNBCs, 2/68 colon carcinomas, and 2/44 glioblastomas (FIGS. 1 and 2). In contrast, this amplicon was absent in $ER^+$ (n=8) and $HER2^+$ (n=15) breast tumors, and in pancreatic ductal adenocarcinomas (n=150). The shortest region of overlap (SRO) spanned 777 kb and included the PD-1 ligands (PD-L1 and PDL2) and the Janus kinase 2 (JAK2) loci (FIG. 3). The height of this recurring amplicon included mean log2ratios>4 consistent with amplification of genomic drivers such as HER2 and MYC described in breast cancer and other solid tumor genomes (FIG. 4).

In order to determine the effect of the PDJ amplicon on JAK2, PD-L1, and PD-L2 expression, 31 TNBC samples were selected; 16 of which were profiled for both copy number analysis and for qRT-PCR analysis. A pooled sample containing unrelated normal breast tissue, individual TNBC, $ER^+$, and $HER2^+$ tumor tissues were used to generate a standard curve for assaying JAK2, PD-L1, and PD-L2 expression. Tumors with a high level amplicon (4/16 TNBCs surveyed by qRT-PCR) had significantly higher expression of JAK2 and PD-L1 genes compared to those without the amplicon (FIG. 2). The latter included samples with low level copy number gains (log2ratio>0 and <1) at 9p24.1 including increases of whole 9p arm and polysomy of chromosome 9. In addition, another TNBC with concurrent elevated expression of JAK2 and PD-L1 was identified in the subset of 15 tumors without aCGH data (FIG. 5). PD-L2 expression also was elevated in the presence of the PDJ amplicon, however, it did not reach statistical significance (p<0.0645).

Clinical data was available on 36 of 41 (88%) of the TNBC patients that were flow sorted then profiled for copy number (FIG. 6). Patients with the high level PDJ amplicon (n=8) were noted to have larger tumors (mean 3.9 cm vs. 1.9 cm, p=0.04) and a higher incidence of lymph node metastases (75% vs. 26%, p=0.01). Lymphocytic infiltration was noted in 4 of the 36 patients, none of whom had the PDJ amplicon in their tumor genome. Twenty nine of these 36 TNBC patients received chemotherapy after definitive surgical therapy. The recurrence rate at 5 years was 70.8% in the PDJ amplified patients, and 29.9% in the unamplified patients (p=0.01). The disease-free survival rate at 5 years was 25% in the PDJ amplified patients, and 66% in the unamplified patients (p=0.005) (FIG. 10). Overall survival (OS) at 5 years was 25% in the PDJ amplified patients, compared with 69% in the unamplified patients (p=0.004) (FIG. 10).

These results indicate that a focal amplification of chromosome 9p24.1 involving PD-L1, PD-L2, and JAK2 occurs in a significant proportion of TNBCs. These results also demonstrate that the presence of the PDJ amplicon defines a clinically significant subset of high-risk TNBC patients. In addition, there results demonstrate that cancer patients with cancer cells that do not express clinically significant levels of the ER, PgR, and HER2 and contain an amplified PDJ amplicon can be treated with a combination of (a) one or more PD-L1 inhibitors and one or more JAK2 inhibitors, (b) one or more PD-1 inhibitors and one or more JAK2 inhibitors, or (c) one or more PD-L1 inhibitors, one or more PD-1 inhibitors, and one or more JAK2 inhibitors.

Example 2—Detecting Cancer Cells Having a PD-L1/PD-L2/JAK2 Amplification

Centromere specific probes such as Vysis CEP3 (Spectrum Red) and Vysis CEP7 (Spectrum Green) (Vysis Inc., Abbott Laboratories, Downers Grove, Ill.) are used to determine centromere copy numbers. For PD-L1 and JAK2 gene copy analysis, FISH probes mapped to chromosome 9p24.1-ptel (http://genome.ucsc.edu/cgi-bin/hgTracks?db=hg19&position=chr9%3A1-7293900&hgsid=418127357_EATu0-e1D1kthxmtWC3SmnkeHoWie) and the Vysis CEP9 (Spectrum Green) are used. Before hybridization, slides are treated according to the Paraffin Pretreatment Reagent Kit protocol (Vysis). Hybridization and post-hybridization washes are performed according to the Vysis LSI procedure. Images are obtained by usage of a Zeiss Axioplan 2 or similar fluorescence microscope (Zeiss, Feldbach, Switzerland) equipped with an ISIS-digital or equivalent camera (MetaSystems, Altlussheim, Germany). All FISH images are acquired with a 100× objective (Plan-Apochromat, Zeiss).

Example 3—Treating Cancer Patients Having $ER^-$/$PgR^-$/$HER2^-$ Cancer Cells Having a PD-L1/PD-L2/JAK2 Amplification Patients with tumors with PD-L1/PD-L2/JAK2 amplification are treated using PD-1, PD-L1, PD-L2, and/or JAK2 inhibitors or targeted immunotherapy of PD-1, PD-L1, PD-L2, and/or JAK2 inhibition. Such treatments are administered alone or in combination with immunotherapy (e.g., vaccine or CTLA-4 blockade) and/or chemotherapy (cyclophosphamide (about 600 $mg/m^2$ every three weeks for four cycles), docetaxel (about 75 $mg/m^2$ every three weeks for four cycles), doxorubicin (about 60 $mg/m^2$ every 2-3 weeks for four cycles), cyclophosphamide (about 600 $mg/m^2$ every three weeks for four cycles), paclitaxel (about 175 $mg/m^2$ every two weeks for four cycles, or about 80 $mg/m^2$ weekly for 12 weeks), cisplatin, carboplatin, gemcitabine, and/or targeted PARP inhibitors).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method for treating a mammal having high risk breast cancer lacking expression of ER, PgR, and HER2, wherein said method comprises:
(a) detecting a copy number amplification of PD-L1 genomic nucleic acid, PD-L2 genomic nucleic acid, and JAK2 genomic nucleic acid in breast cancer cells of said breast cancer,

(b) administering a PD-1 inhibitor or PD-L1 inhibitor to said mammal, and (c) administering a JAK2 inhibitor to said mammal.

2. The method of claim 1, wherein said mammal is a human.

3. The method of claim 1, wherein said method comprises administering said PD-1 inhibitor to said mammal.

4. The method of claim 3, wherein said PD-1 inhibitor is pembrolizumab, nivolumab, MEDI0680 (AMP-514), or CT-011 (pidilizumab).

5. The method of claim 1, wherein said method comprises administering said PD-L1 inhibitor to said mammal.

6. The method of claim 5, wherein said PD-L1 inhibitor is MPDL3280A, MSB0010718C, MEDI4736, or BMS-936559.

7. The method of claim 1, wherein said JAK2 inhibitor is ruxolitinib or pacritinib.

* * * * *